United States Patent [19]

Miller et al.

[11] Patent Number: 4,779,973

[45] Date of Patent: Oct. 25, 1988

[54] PHOTOKERATOMETRIC DEVICE

[76] Inventors: David Miller, 9 Francis St., Brookline, Mass. 02146; Hiroyuki Ohtsuka; Hirofumi Matsuzawa, both of c/o Tokyo Kogaku Kikai Kabushiki Kaisha 75-1, Hasunuma-cho, Itabashi-ku, Tokyo, 174, Japan; Paul R. Cotran, 9 Highrock Way #2, Allston, Mass.

[21] Appl. No.: 927,390

[22] Filed: Nov. 6, 1986

[51] Int. Cl.⁴ ............................................. A61B 3/10
[52] U.S. Cl. .................................... 351/212; 351/214
[58] Field of Search ...................... 351/212, 214, 247; 350/523, 528, 235

[56] References Cited

U.S. PATENT DOCUMENTS 3,290,927  12/1966  Gambs ................................ 351/212
3,932,030   1/1976  Hasegawa et al. ................ 351/212
4,046,463   9/1977  La Rassa et al. .................. 351/212
4,196,980   4/1980  Heine ................................. 351/212
4,236,781  12/1980  Arimura ............................. 350/235

Primary Examiner—Rodney B. Bovernick
Assistant Examiner—Jay Ryan
Attorney, Agent, or Firm—Finnegan, Henderson, Farabow, Garrett and Dunner

[57] ABSTRACT

A photokeratometric device for attachment to a photoslit lamp microscope having a light source therein comprises a keratometric pattern plate having an opening in the center thereof and a mount for supporting the plate for reproducing through the microscope an image of the cornea of a patient being examined with the keratometric pattern superimposed thereon.

11 Claims, 5 Drawing Sheets

PHOTOKERATOMETRIC DEVICE

BACKGROUND OF THE INVENTION

The present invention relates to a photokeratometric device for attachment to a photoslit lamp microscope and, more particularly, to a photokeratometric device mounted on a photoslit lamp microscope for measuring the curvature radius, shape and optical characteristics of the cornea of an eye under examination.

A photokeratometer has been disclosed in the prior art in which a coaxial annular pattern, referred to as a Placido pattern, is projected on the cornea of an eye under examination and a photograph of an image reflecting from the cornea is taken. The photograph is photodensitometrically measured to obtain data, e.g., the curvature radius, shape and optical characteristics of the cornea. Since a photokeratometer is normally an independent ophthalmic instrument, it cannot readily be mounted on a photoslit lamp microscope.

A hand held Placido pattern disc also has been known in the ophthalmic field. This Placido pattern disc includes a plurality of LEDs (light emitting diodes) arranged thereon to project a Placido pattern on the cornea. An image reflected from the cornea is observed through an ophthalmoscope.

In photographing the cornea image, however, it has been difficult to properly position a Placido disc and therefore it has not been possible previously to use a Placido disc in photokeratometry.

SUMMARY OF THE INVENTION

An object of the present invention is to overcome the difficulties of conventional keratometry devices and to provide an attachment which can be detachably mounted on a photoslit lamp microscope.

Another object of the present invention is to provide an attachment to which a light source unit, a microscope unit, or a photographing unit of a photoslit lamp microscope can be applied.

Still another object of the present invention is to provide an attachment for adding a photokeratometric function to a photoslit lamp microscope.

According to the present invention, there is provided a photokeratometric device for attachment to a photoslit microscope including a microscope unit and a light source unit therein, comprising a Placido pattern plate having an opening in its center, and means for supporting the plate for reproducing through the microscope an image of the cornea of a patient being examined with the keratometric pattern superimposed thereon. When the support means mounts the attachment on the microscope unit, the pattern plate is placed in front of the eye at a preset distance from the eye and light from the light source unit is projected onto the eye through the pattern plate.

A photokeratometric device for attachment to a photoslit lamp microscope of the present invention has an advantage in that photokeratometry may be carried out by using a microscope unit and a light source unit of a photoslit lamp microscope.

Further objects and advantages of the present invention will be best understood from the description of specific embodiments with reference to the accompanying drawings.

DESCRIPTION OF THE PREFERRED EMBODIMENTS

"A Photoslit Lamp Microscope" in the specification shall refer to, but is not limited to, a slit lamp in which an observation image is recorded, for example, on a film by a 35 mm camera or a Polaroid instant camera, or an observation image is converted into an electronic signal by an image pick-up tube which in turn is electronically or electromagnetically stored in a memory.

"A Keratometric Pattern" as used herein refers to, but is not limited to, a Placido pattern having a plurality of coaxial circles or a pattern formed by a combination of coaxial circles and radial lines.

Figure 1:
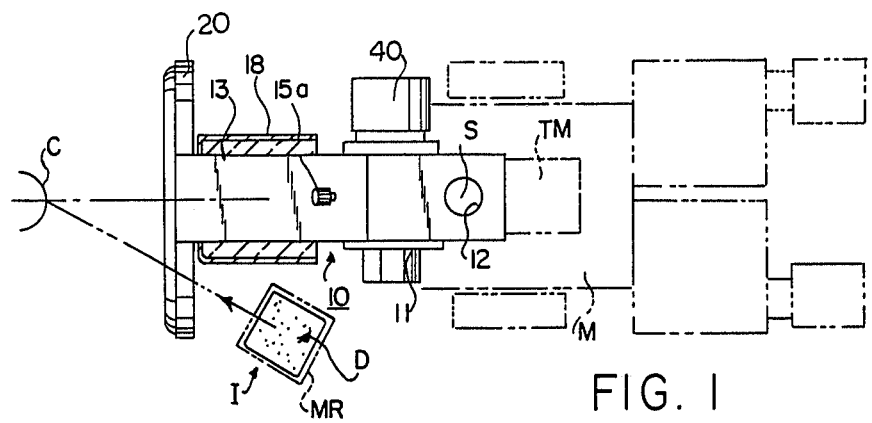
FIG. 1 is a plane view of an attachment of the present invention.
Figure 2:
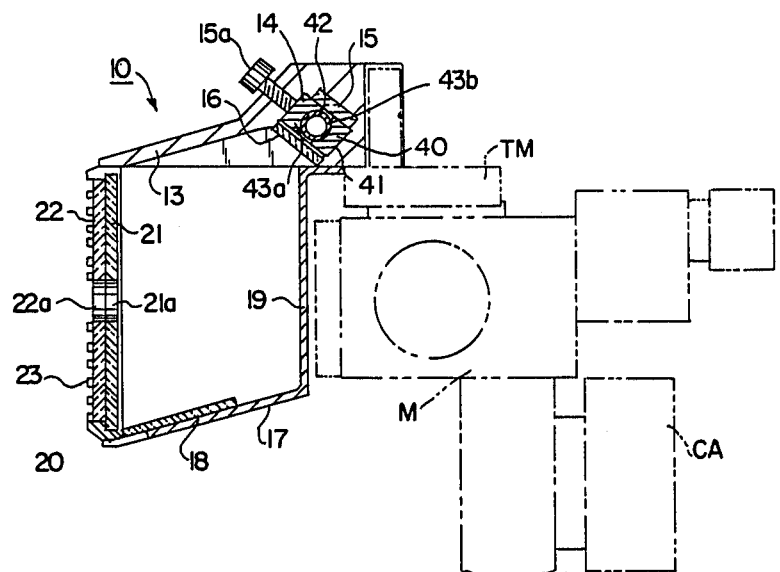
FIG. 2 is a sectional view of the attachment shown in FIG. 1.

As illustrated in FIGS. 1 and 2, a support frame 10 is provided with a mounting member 11. A bearing 12 of the mounting member 11 is sized for receiving a shaft of a tonometer mounting member TM of an aplanation tonometer. The tonometer is attached to a microscope unit M of a photoslit lamp microscope by the mounting member TM. An arm 13 extending from the mounting member 11 has a ring member 20 at a front end thereof. A diffuser plate 21 and a Placido pattern plate 22 are fixed in the ring member 20 with the Placido pattern plate 22 disposed in front of the diffuser plate 21, as shown in FIG. 2. The diffuser plate 21 has a glass base layer with powdery sand deposited on both the surfaces thereof. The pattern plate 22 is made of glass plate. On one side of the glass plate, a diffuser surface is formed by depositing powdery sand, and on the other side, a Placido pattern 23 with coaxial, equally spaced circles is formed by a vacuum vapor method. The diffuser plate 21 and the pattern plate 22 each have a coaxial circular opening in the center thereof, the opening being substantially aligned to form an observation passage through the plates 21 and 22. Light from a light source unit of the photoslit lamp, which includes both an observation light source unit and a photographing light source unit in a conventional manner is projected onto an eye under examination through the diffuser plate 21 and the pattern plate 22, and an image formed by light reflecting from the cornea is observed through an objective lens of the microscope unit, as hereinafter described in more detail. If light from the photographing light source of a photoslit lamp microscope is bring enough to illuminate the pattern 23 through the diffuser plate 21 uniformly, an image reflecting from the cornea may be photographed or otherwise recorded.

As shown in FIGS. 1 and 2, a photographing light source unit 40 is removably set in the mounting member 11. Some photoslit lamp microscopes, such as the TOPCON Photoslit Lamp Model SL-6E manufactured by Tokyo Optical Co., Ltd., the assigned of the present patent application, have a removable xenon flash lamp unit as a photographing light source unit. These units also can be used as the photographing light source unit 40. Normally, the light from the light source in a photoslit lamp microscope is insufficient to photograph the entire cornea for photokeratometry. However, with present invention, photokeratometry can be carried out even though the intensity of light from a photographing light source unit of a photoslit lamp microscope is relatively low.

A lamp receiving perforation 14 parallel to the ring member 20 is formed in the mounting member 11. A xenon lamp unit 40 is inserted into the receiving perforation 14 and is fixed by a stop screw 15a. The lamp unit 40 consists of a frame 41 having apertures 43a and 43b and a xenon lamp 42 supported by the frame 41. Light from the lamp 42 is radiated through the apertures 43a and 43b. In the inner surface of the perforation 14, a mirror 15 is arranged to reflect the light passing through the aperture 43b from the xenon lamp 42.

Figure 3:
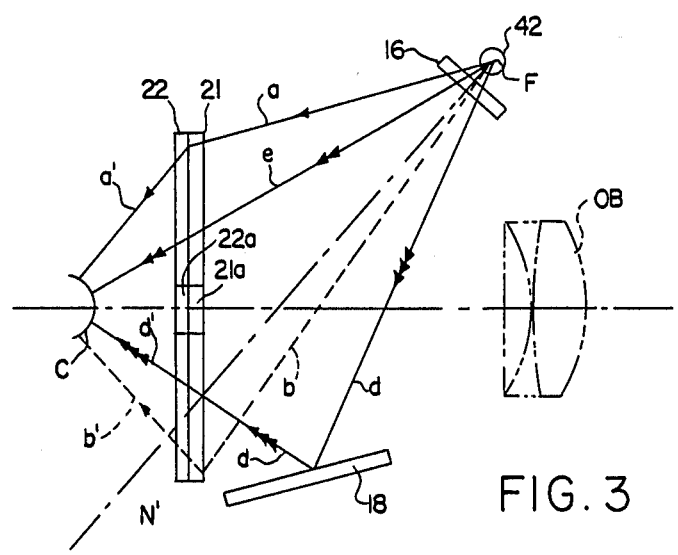
FIG. 3 illustrates light rays projected onto the cornea.

A diffuser plate 16 is provided on the opposite side to the mirror 15 in the inner surface of the perforation 14 to diffuse light passing through the aperture 43a from the xenon lamp 42 and the light reflecting from the mirror 15 and passing through the aperture 43b, the xenon lamp 42, and the aperture 43a, respectively. As shown in FIG. 3, a normal line N stemming from the luminance point F of the xenon lamp 42 and passing through the diffuser plate 16 passes through a point located at a predetermined distance below the openings 21a and 22a.

With this arrangement, the intensity of incident light rays to the photographing unit (not shown) through the microscope unit, especially, that of light rays a, a' and e coming from the xenon lamp 42 and reflecting from the cornea c, is made uniform.

Figure 4:
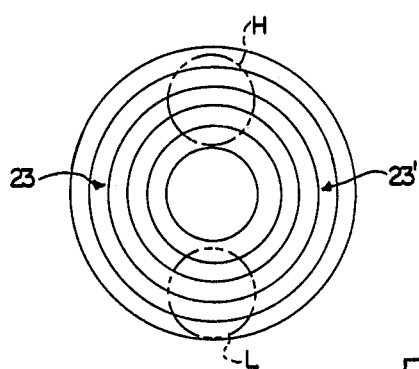
FIG. 4 shows a projected Placido image.

In the present embodiment, since the xenon lamp 42 is located in a position slightly above and at an oblique angle to the pattern 23, the most intensive incident light ray to the photographing unit is a light ray reflecting from the cornea c in response to the light ray e, as shown in FIG. 3 (where reflecting light rays from the cornea are not shown for the sake of avoiding complexity). Light rays reflecting from cornea c in response to the light rays a and a' (light ray components diffused by the diffuser plate 21) are relatively low in intensity, and those reflected from the cornea c in response to the light rays b and b' (a light ray component diffused by the diffuser plate 21) are very low in intensity. As a result, a projected pattern image 23' has a bright upper area H and a dark lower area L, as shown in FIG. 4.

In order to overcome this disadvantage, a mirror 18 is mounted on an inclined supporting plate 17 (FIG. 2) of the frame member 10 to reflect light rays d (below the light rays e) which would otherwise not intersect the plate 21. These rays d are in turn diffused by the diffuser plate 21, and diffused light rays d' increase the intensity of reflecting light rays from the cornea c to make a reflected pattern image 23' more uniformly bright.

Further, in order to prevent incident light which is emitted from the xenon lamp 42 and reflected partially by the diffuser plate 21 from functioning as ghost light to the microscope, a light shielding plate 19 is provided between the mounting member 11 and the mirror supporting plate 17.

Figure 5:
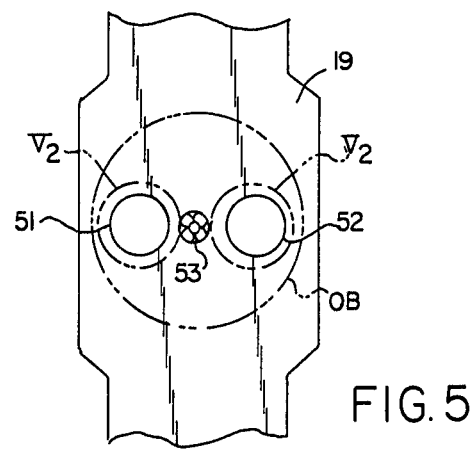
FIG. 5 shows a light shielding plate of the attachment.

In addition, the shielding plate 19 has a pair of apertures 51 and 52 and a fixation target 53. The apertures 51 and 52 are provided on the plate 19 as shown in FIG. 5 to guide the observation pattern of light rays which are reflected from the cornea and which pass through the openings 21a and 22a to the objective lens OB of the microscope unit M and binocular observation units V1 and V2. The fixation target 53 is provided at a central point located between the apertures 51 and 52. The fixation target 53 may be a white circle or a light emitting diode at which a patient can look to fix the visual line.

In the photoslit lamp microscope, light from the light source unit is obliquely projected to the eye under examination by way of mirror MR (FIG. 1) and observation of the light reflected from the cornea is carried out through the microscope unit M. In a preferred embodiment, however, since it is necessary to illuminate the pattern 23 by diffused light, the mirror MR further includes a diffuser plate D set thereon, as shown in FIG. 1.

An operation of the attachment for a photoslit lamp microscope will be explained hereinbelow.

According to a preferred embodiment of the present invention, the attachment is mounted on the photoslit lamp microscope through the tonometer mounting member TM and the pattern plate 22 is placed at a preset distance from the objective lens OB of the microscope unit M. Diffused illumination light from the mirror MR and the diffuser plate D is obliquely projected to the eye through the pattern plate 22, as shown in FIG. 1. Light reflected from the cornea passes through the openings 21a and 22a and reaches the microscope unit M so that keratometric observation can be carried out.

Prior to photographing, the xenon lamp unit 40 is removed from the light source unit of the photoslit lamp microscope and is inserted into the receiving perforation 14. When the xenon lamp unit 40 is energized, some light rays therefrom directly reach the diffuser plate 21, while other light rays reach the diffuser plate 21 by reflection from the mirror 18. Accordingly, uniformly diffused illumination light is projected to the eye through the pattern 23. Light reflected from the cornea passes through the openings 21a and 22a, the apertures 51 and 52 and the microscope unit M, so that the pattern image 23' and the front of the eye are photographed by the photographing unit of the photoslit lamp microscope.

Figure 6:
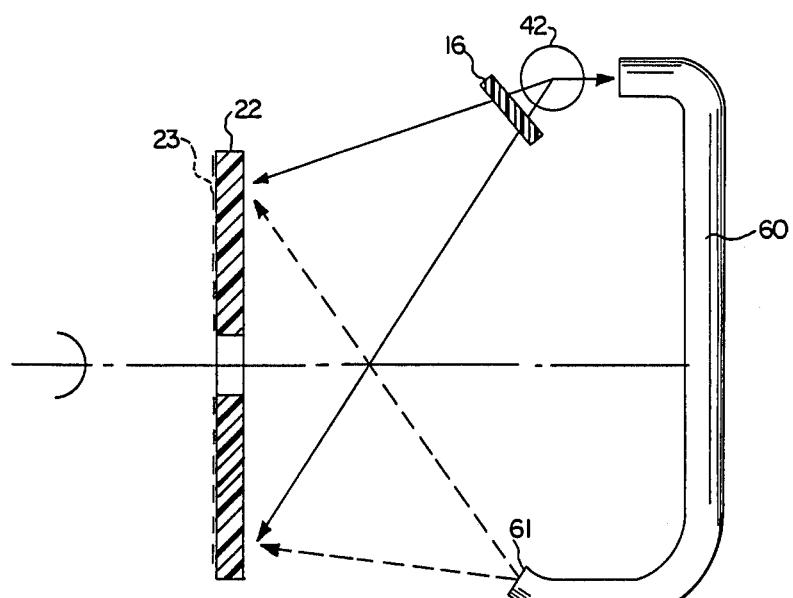
FIG. 6 schematically illustrates a second embodiment of the present invention.

As shown in FIG. 6, the mirror 18 may be replaced by optical fibers 60. The exit end 61 of the optical fibers 60 is arranged obliquely to the plate 22 to project light supplied at the entrance from the flash lamp 42 onto the pattern plate 22. The pattern plate 22 is made of a highly diffusive plastic disc on the front surface of which the Placido pattern 23 is printed by a silky printing method.

Figure 7:
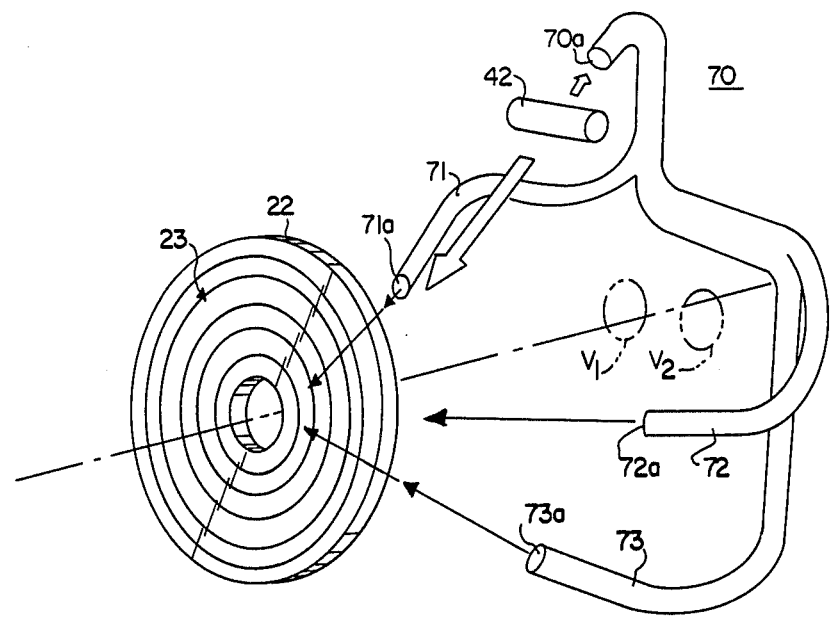
FIG. 7 schematically illustrates a third embodiment of the present invention.

The embodiment shown in FIG. 7 is a modification of the embodiment illustrated in FIG. 6 in which optical fibers 70 have one input portion 70a and three branch portions 71, 72 and 73. Light emitted from the flash lamp 42 is directly projected onto the pattern plate 22 and is supplied to the entrance end 70a of the optical fibers 70. Illumination light is projected from the exit ends 71a and 72a of the branch portions 71 and 72 on the right and left sides of the pattern plate 22, respectively, and the exit end 73a of the branch portion 73 on the lower side of plate 22. Therefore, the pattern plate 22 is uniformly illuminated.

Figure 8:
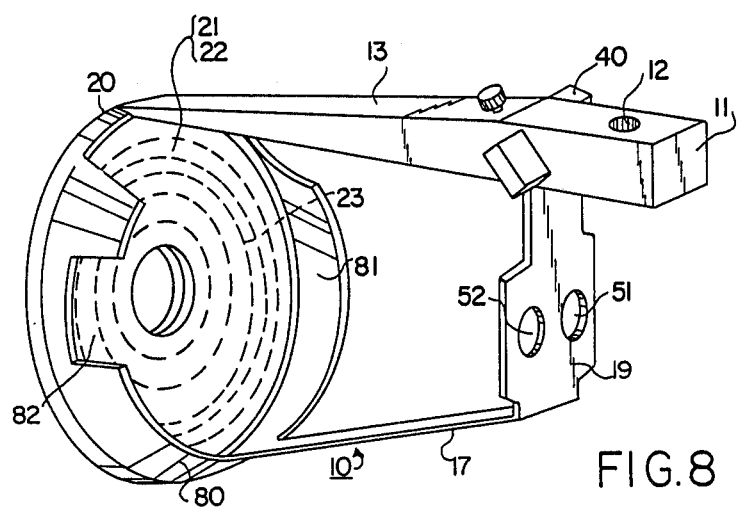
FIG. 8 is a perspective view of a fourth embodiment of the present invention.

In the embodiment shown in FIG. 8, the ring member 20 is provided with a cone shaped extension 80 having a cut-out portion 82. The inner surface 81 of the extension 80 has white or milky white diffusing paint thereon. The cut-out portion 82 is provided in order for light from the light source unit of the photoslit lamp microscope to pass therethrough. Light from both the xenon lamp unit 40 and the light source unit is diffused by and reflected from the inner surface 81 so that it can illuminate the diffuser plate 21 uniformly.

Figure 9:
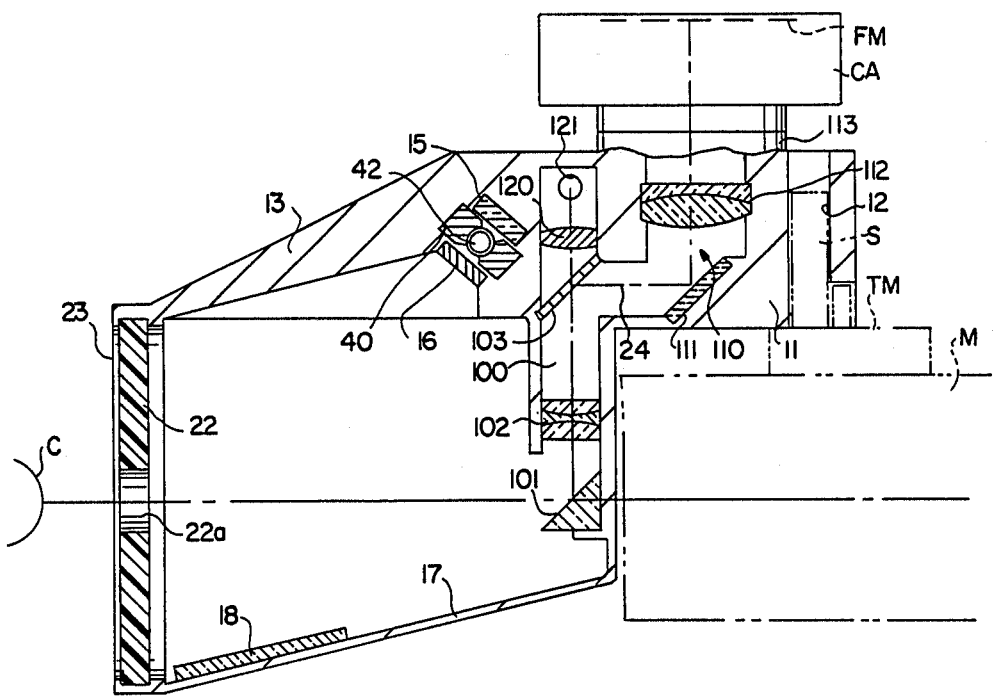
FIG. 9 shows a sectional view of the attachment in accordance with a fifth embodiment of the present invention.

FIG. 9 shows another preferred embodiment of the present invention which is applied to a slit lamp microscope having no photographing unit. The mounting member 11 includes a tube 100 and a camera supporting tube 110 therein. A mirror 101, an image forming lens 102, a half mirror 103, a condenser lens 120 and a fixation target lamp 121 are arranged in the tube 100. A mirror 111 and a relay lens 112 are arranged in the camera supporting tube 110, which supports a camera CA at the upper end thereof. The camera CA has a film FM. Except for these components, the mounting member 11 is the same in structure as that of the embodiment illustrated in FIGS. 1 and 2.

The attachment is mounted on the tonometer mounting member of the slit lamp microscope. When the fixation target lamp 121 is turned on, light therefrom is made parallel through the lens 120, the half mirror 103 and the image forming lens 102. The parallel light is projected onto an eye under examination through the opening 22a. A patient gazes at the image of the fixation target lamp and fixes the visual line.

In the photographing operation, photographing light from the xenon lamp unit 40 is projected onto the eye through the pattern plate 22 as in the first embodiment. Light reflected from the cornea passing through the opening 22a is reflected from the mirror 101, and intermediate images 24 of the reflected pattern and the cornea are formed by the image forming lens 102 and the half mirror 103. The images 24 are in turn formed on the film FM of the camera CA by the mirror 111 and the relay lens 112.

As explained hereinabove in detail, the attachment for a photoslit lamp microscope of the present invention has advantages in that it is quite simple in structure is inexpensive, and photokeratometry may be carried out by using a microscope unit and a light source unit of a photoslit lamp microscope.

What we claim is:

1. A photokeratometric device for attachment to a photoslit lamp, said photoslit lamp including microscope means for observing an image of an eye under examination, recording means for recording an image of the eye, and illumination means including observation light source means for illuminating the eye when the image of the eye is observed by the microscope and removable recording light source means for illuminating the eye when the image of the eye is recorded by the recording means, said photokeratometric device comprising:
   a keratometric patter plate having a Placido pattern thereon and having an opening in the center thereof through which observation light from said observation light source means may be transmitted;
   attachment means for attaching said keratometric pattern plate to said photoslit lamp, said attachment means including
      an arm member having a first end and a second end,
      mounting means disposed at said first end of said arm member, and
      holding means for holding said keratometric pattern plate at said second end of said arm member;
   said mounting means being detachably mounted on the microscope means so as to position said keratometric pattern plate a predetermined distance in front of the microscope means; and
   said Placido pattern being projected onto the cornea of the eye under examination by illumination of observation light from said observation light source means when an image of said Placido pattern reflected from the cornea is observed by the microscope means through said opening.

2. The photokeratometric device of claim 1 wherein said holding means further includes diffusing means for diffusing the observation light and the recording light.

3. The photokeratometric device of claim 1 wherein said mounting means mounts the recording light source means thereon when the image of said Placido pattern reflected from the cornea is recorded by said recording means.

4. The photokeratometric device of claim 1 wherein said attachment means further includes light guiding means disposed at a peripheral portion of said keratometric pattern plate for guiding at least a part of the recording light toward said keratometric pattern plate.

5. The photokeratometric device of claim 4 wherein said attachment means further includes a support plate and said light guiding means includes reflective means supported by said support plate for reflecting at least part of the recording light from the recording light source.

6. The photokeratometric device of claim 5 wherein said reflective means is a mirror.

7. The photokeratometric device of claim 5 wherein said support plate includes fixation target means for fixing the vision of a patient to be examined.

8. The photokeratometric device of claim 5 wherein said support plate includes aperture means for observing and recording the image of said Placido pattern therethrough by said microscope means and said recording means.

9. The photokeratometric device of claim 1 further comprising a tonometer mount provided on said microscope means, said attachment means being mounted on the tonometer mount by said mounting means.

10. The photokeratometric device of claim 1 wherein said recording light source means is a removable xenon lamp.

11. The photokeratometric device of claim 10 wherein said mounting means includes slot means for removably mounting said xenon lamp, and said xenon lamp includes a housing permitting attachment of said xenon lamp to either of said slot means and said illumination means.

* * * * *